(12) United States Patent
Yamanashi et al.

(10) Patent No.: US 12,185,919 B2
(45) Date of Patent: Jan. 7, 2025

(54) ENDOSCOPE APPARATUS AND METHOD OF OPERATING ENDOSCOPE APPARATUS

(71) Applicant: OLYMPUS CORPORATION, Tokyo (JP)

(72) Inventors: Momoko Yamanashi, Tachikawa (JP); Kazuhiko Hino, Hachioji (JP); Takeo Suzuki, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 798 days.

(21) Appl. No.: 17/023,780

(22) Filed: Sep. 17, 2020

(65) Prior Publication Data

US 2021/0076913 A1    Mar. 18, 2021

Related U.S. Application Data

(63) Continuation of application No. PCT/JP2019/003003, filed on Jan. 29, 2019.

(30) Foreign Application Priority Data

Mar. 20, 2018   (JP) ................................. 2018-052514

(51) Int. Cl.
    *A61B 1/015*      (2006.01)
    *A61B 1/00*        (2006.01)
    (Continued)

(52) U.S. Cl.
CPC .......... *A61B 1/015* (2013.01); *A61B 1/00082* (2013.01); *A61B 1/00089* (2013.01);
(Continued)

(58) Field of Classification Search
CPC ..... A61B 1/012; A61B 1/015; A61B 1/00082; A61B 1/31; A61B 1/00135; A61B 1/00142; A61B 1/00154
See application file for complete search history.

(56) References Cited

U.S. PATENT DOCUMENTS 4,445,892 A * 5/1984 Hussein ............. A61B 1/00082
606/7
4,824,436 A * 4/1989 Wolinsky ............ A61M 25/104
604/509

(Continued)

FOREIGN PATENT DOCUMENTS

| JP | 2011-198077 A | 7/2001 |
| JP | 2008-262089 A | 10/2008 |
| WO | 2012/122288 A2 | 9/2012 |

OTHER PUBLICATIONS

International Search Report dated Mar. 26, 2019 received in PCT/JP2019/003003.

*Primary Examiner* — Ryan N Henderson
(74) *Attorney, Agent, or Firm* — Scully, Scott, Murphy & Presser, P.C.

(57) ABSTRACT

An endoscope apparatus includes: an insertion section; a flow passage; a closed space forming member configured to form a closed space in at least a portion of an intestine; a pump configured to apply pressurization and depressurization to a liquid in the closed space a plurality of times through the flow passage in a state where the liquid is retained in the closed space; a flow passage allowing the liquid in the closed space to which the pressurization and the depressurization are applied the plurality of times through the flow passage to flow out to an outside of the intestine, and a liquid discharge opening.

18 Claims, 11 Drawing Sheets

(51) Int. Cl.
   *A61B 1/018* (2006.01)
   *A61B 1/12* (2006.01)
   *A61B 1/31* (2006.01)

(52) U.S. Cl.
   CPC .............. *A61B 1/018* (2013.01); *A61B 1/126* (2013.01); *A61B 1/31* (2013.01)

(56) References Cited

U.S. PATENT DOCUMENTS

| | | | | |
|---|---|---|---|---|
| 4,911,163 | A * | 3/1990 | Fina ................... | A61M 25/1011 604/908 |
| 7,399,290 | B2 * | 7/2008 | Maki ..................... | A61M 27/00 604/96.01 |
| 8,348,891 | B2 * | 1/2013 | Sugahara ........... | A61B 17/0057 604/103.05 |
| 9,205,234 | B2 * | 12/2015 | Hardin ............... | A61M 25/1011 |
| 10,799,092 | B2 * | 10/2020 | Krimsky ............ | A61B 1/00085 |
| 11,071,557 | B2 * | 7/2021 | Lawinger ........... | A61B 17/2202 |
| 11,877,722 | B2 * | 1/2024 | Milsom ............. | A61B 1/00082 |
| 2005/0020976 | A1 * | 1/2005 | Maki ................... | A61M 25/1011 604/96.01 |
| 2007/0015965 | A1 * | 1/2007 | Cox .................... | A61B 1/00078 600/116 |
| 2009/0118582 | A1 * | 5/2009 | Tsumaru ............ | A61B 1/00094 600/114 |
| 2011/0105845 | A1 * | 5/2011 | Gordon ................ | A61B 1/273 600/156 |
| 2011/0125132 | A1 * | 5/2011 | Krolik ............. | A61M 25/10185 604/509 |
| 2011/0190584 | A1 * | 8/2011 | Sugahara ........... | A61M 25/1011 600/116 |
| 2012/0259216 | A1 * | 10/2012 | Gerrans ......... | A61B 17/320725 604/514 |
| 2012/0259217 | A1 * | 10/2012 | Gerrans .......... | A61M 25/10181 604/514 |
| 2012/0302953 | A1 * | 11/2012 | Don Michael ......... | A61B 17/22 604/101.05 |
| 2013/0261544 | A1 * | 10/2013 | Hardin ............... | A61M 25/1011 604/101.05 |
| 2016/0074581 | A1 * | 3/2016 | Gerrans ............... | A61B 5/0215 600/301 |
| 2016/0287055 | A1 * | 10/2016 | Kesten ................. | A61M 25/10 |
| 2017/0281912 | A1 * | 10/2017 | Melder ................ | A61K 31/337 |
| 2018/0078119 | A1 * | 3/2018 | Krimsky ............ | A61B 1/00085 |
| 2019/0000429 | A1 * | 1/2019 | Magana ............. | A61M 25/0113 |
| 2021/0000330 | A1 * | 1/2021 | Krimsky ............ | A61M 25/1011 |

* cited by examiner

ENDOSCOPE APPARATUS AND METHOD OF OPERATING ENDOSCOPE APPARATUS

CROSS REFERENCE TO RELATED APPLICATION

This application is a continuation application of PCT/JP2019/003003 filed on Jan. 29, 2019 and claims benefit of Japanese Application No. 2018-052514 filed in Japan on Mar. 20, 2018, the entire contents of which are incorporated herein by this reference.

BACKGROUND OF THE INVENTION

1. Field of the Invention

The present invention relates to an endoscope apparatus where a flow passage which communicates with an inside of an object and allows a liquid to flow into the object is provided to an insertion section, and a method of operating the endoscope apparatus.

2. Description of the Related Art

Recently, the endoscope has been popularly used in a medical field and an industrial field. The endoscope can observe an inside of an object by inserting an elongated insertion section into the object.

A configuration of an endoscope is well-known where, to ensure a favorable observation field of view in an object, a fluid is supplied from an opening of a fluid supply conduit, formed on a distal end portion positioned on a distal end side of an insertion section in a longitudinal direction (hereinafter, simply referred to as a distal end side), in a direction in a longitudinal direction, that is, toward a region in front of the opening in the longitudinal direction in a state where the insertion section is inserted into the object.

More specifically, the configuration of an endoscope apparatus is well-known where a fluid is made to flow from a fluid supply device into a fluid supply conduit disposed in an endoscope, and the fluid is supplied to waste adhering to a wall surface of an object from an opening of the fluid supply conduit so as to remove the waste from the wall surface. Examples of the fluid include air, a liquid, and a mixture of air and a liquid.

The configuration of an endoscope apparatus is also well-known where, using a suction conduit to which a suction device is connected and which is disposed in an endoscope, waste removed by supplied fluid from a wall surface is sucked from an opening formed on a distal end portion of the suction conduit.

In performing such observation by inserting an insertion section into a large intestine using an endoscope for medical use, for example, there may be a case where a large amount of food residue remains in the large intestine due to reasons such that a subject forgets to take a laxative, does not observe restriction on food, or has an emergency symptom.

In view of such circumstances, Japanese Patent Application Laid-Open Publication No. 2001-198077 discloses a configuration of an endoscope apparatus where, to ensure a favorable observation field of view, waste on a mucous membrane in a large intestine is removed by repeating a supply of a fluid to a food residue in an object from a fluid supply conduit and a suction of the fluid and the food residue through the suction conduit and, then, an inspection, a treatment and the like are performed.

SUMMARY OF THE INVENTION

According to an aspect of the present invention, there is provided an endoscope apparatus including: an insertion section configured to be inserted into an object from a distal end side of the insertion section in a longitudinal direction; a flow passage formed in the insertion section, the flow passage communicating with an inside of the object, the flow passage allowing a liquid to flow into the object through the flow passage; a closed space forming member configured to form a closed space in at least a portion in the object such that the liquid is retained in the object; a pump configured to apply pressurization and depressurization to the liquid in the closed space a plurality of times through the flow passage in a state where the liquid is retained in the closed space; and a fluid discharge passage allowing the liquid in the closed space to which the pressurization and the depressurization are applied the plurality of times through the flow passage to flow out to an outside of the object.

According to another aspect of the present invention, there is provided a method of operating an endoscope apparatus including: inserting an insertion section into an object from a distal end side in a longitudinal direction; forming a closed space in at least a portion of the object by a closed space forming member such that the liquid is retained in the object; allowing the liquid to flow into the closed space through a flow passage which is formed in the insertion section and communicates with the inside of the object; retaining the liquid in the closed space; performing pressurization and depressurization of the liquid in the closed space a plurality of times by a pump in a state where the liquid is retained in the closed space; and allowing the liquid retained in the closed space to which the pressurization and the depressurization are applied a plurality of times through the flow passage to flow out to an outside of the object through a fluid discharge passage.

DETAILED DESCRIPTION OF THE PREFERRED EMBODIMENTS

Hereinafter, embodiments of the present invention are described with reference to drawings. The drawings are schematic views, and it is noted that a relationship between a thickness and a width of respective members, a ratio of the thickness of each member and the like are different from corresponding relationship, ratio and the like of actual members. It goes without saying that portions with different dimensional relationships and ratios are included in the respective drawings.

In the embodiments described hereinafter, description is made by taking an endoscope apparatus for medical use as one example of an endoscope apparatus.

First Embodiment

Figure 1:
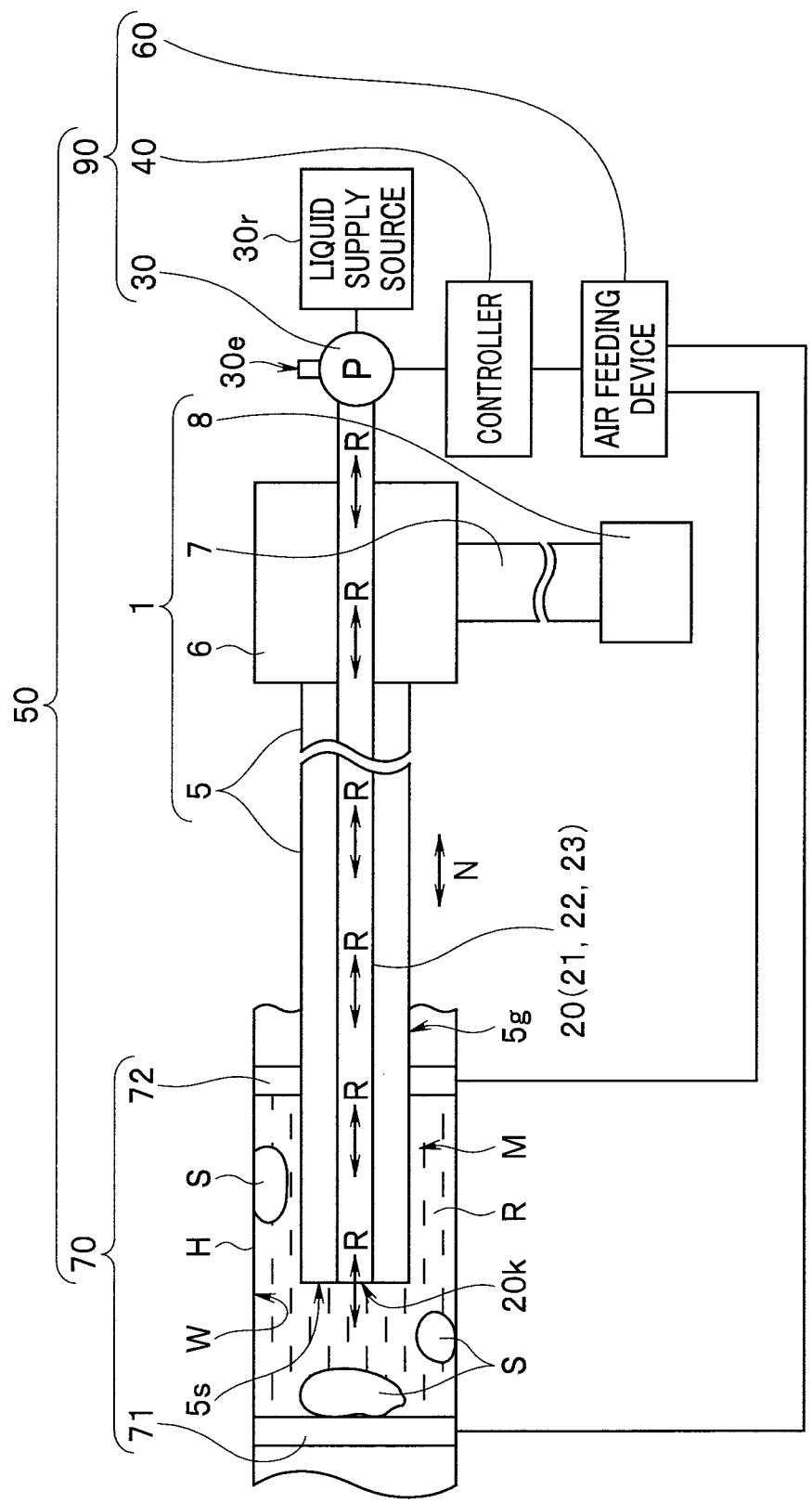
FIG. 1 is a view schematically showing an endoscope apparatus according to a first embodiment in a state where an insertion section of an endoscope is inserted into an object.
Figure 2:
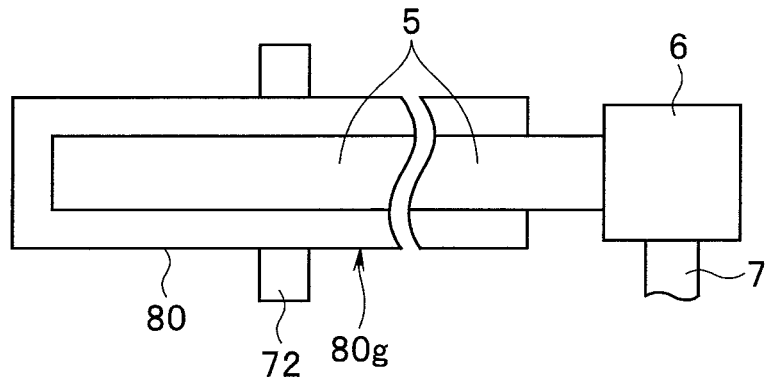
FIG. 2 is a view schematically showing a modification where a balloon shown in FIG. 1 is mounted on a sheath which covers an outer periphery of the insertion section.

FIG. 1 is a view schematically showing an endoscope apparatus according to an embodiment in a state where an insertion section of an endoscope is inserted into an object. FIG. 2 is a view schematically showing a modification where a balloon shown in FIG. 1 is mounted on a sheath which covers an outer periphery of the insertion section.

As shown in FIG. 1, the endoscope apparatus 50 is constituted of an endoscope 1, a closed space forming member 70 and a peripheral device 90.

The endoscope 1 includes: an insertion section 5 which is inserted into, for example, an intestine H of a large intestine which is an object from a distal end side of the insertion section 5; and an operation section 6 which is continuously connected to a proximal end of the insertion section 5 in a longitudinal direction N.

The endoscope 1 further includes: a universal cord 7 which is extended from the operation section 6; and a connector 8 which is provided on an extended end of the universal cord 7.

A flow passage 20 which communicates with an inside of the intestine H, and allows a liquid R for cleaning to flow into the intestine H is formed in the insertion section 5.

In the embodiment, the flow passage 20 is also formed in the operation section 6, and is connected to a pump 30 outside the endoscope 1.

Alternatively, the flow passage 20 may be formed such that the flow passage 20 is formed in the universal cord 7 and the connector 8 and the connector 8 is connected to the pump 30.

A distal end of the flow passage 20 in the longitudinal direction N opens as an opening 20k at a distal end surface 5s of the insertion section 5.

The flow passage 20 injects the liquid R into the intestine H from the opening 20k in a direction in the longitudinal direction N, more specifically, frontward in the longitudinal direction N (hereinafter, simply referred to as "frontward").

The closed space forming member 70 is configured to form a closed space M in at least a portion of the intestine H such that the liquid R injected from the opening 20k is retained in the intestine H.

As one specific example, in the embodiment, the closed space forming member 70 is provided for sealing a region of the intestine H where waste S such as food residues adhere to the intestine H from other portions of the intestine H. The closed space forming member 70 is constituted of balloons 71, 72 which are inflatable and deflatable by drive control using a controller 40.

The balloon 71 is disposed in the intestine H protruding frontward from the distal end surface 5s of the insertion section 5.

More specifically, the balloon 71 is disposed in the intestine H frontward with respect to the distal end surface 5s by way of a balloon catheter which passes through a treatment instrument insertion channel not shown which is formed in the insertion section 5 or the like. Note that other known methods may be used as a method of arranging the balloon 71.

In the embodiment, the balloon 72 is mounted on an outer periphery 5g of the insertion section 5 at a position on a proximal end side in the longitudinal direction N with respect to a distal end side portion of the insertion section 5.

Alternatively, the balloon 72 may be mounted on an outer peripheral surface 80g of a sheath 80 which covers the outer periphery of the insertion section 5 and is inserted into the intestine H with the insertion section 5.

When air is supplied to the balloons 71, 72 from an air feeding device 60 described later by drive control using the controller 40, the balloons 71, 72 are inflated in the intestine H and are brought into contact with an intestine wall W. Accordingly, the balloons 71, 72 form the previously mentioned closed space M in the intestine H. The control of the balloons may be performed by an external air feeding device other than the controller 40 and the air feeding device 60.

The peripheral device 90 includes the pump 30, the controller 40 and the air feeding device 60.

The pump 30 is a pump which can supply air A and a liquid R into the flow passage 20, and is connected to a liquid supply source 30r. The pump 30 has a function of supplying the liquid R from the liquid supply source 30r to the closed space M through the flow passage 20, and of recovering the liquid R from the closed space M toward a liquid discharge opening 30e which constitutes a fluid discharge passage through the flow passage 20.

In a state where the liquid R is retained in the closed space M, the pump 30 automatically performs pressurization and depressurization of the flow passage 20 and the liquid R in the closed space M a plurality of times through the flow passage 20. In other words, the pump 30 is operated so as to make the liquid R for cleaning flow into and out from the closed space M a plurality of times.

In the embodiment, the flow passage 20 is configured to function as; a first flow passage 21 configured to feed a liquid R to the closed space M; a second flow passage 22 used for pressurization and depressurization of the liquid R retained in the closed space M by the pump 30; and a third flow passage 23 configured to discharge the liquid R from the closed space M.

In other words, in the embodiment, the first flow passage 21, the second flow passage 22 and the third flow passage 23 are integrally formed.

In this manner, in the embodiment, one flow passage 20 also functions as the third flow passage 23 which constitutes a fluid discharge passage which allows the liquid R in the closed space M to which the pressurization and the depressurization are applied a plurality of times through the flow passage 20 to flow out to the outside of the object, more specifically, to the outside of the endoscope 1, with the waste S in the closed space M.

The third flow passage 23 may also function as the previously mentioned treatment instrument insertion channel.

The fluid discharge passage may have other configurations provided that the fluid discharge passage can discharge the liquid R in the closed space M to the outside of the object. For example, the fluid discharge passage may be formed in a conduit for suction which is inserted into the sheath 80 (described previously) with the insertion section 5.

The controller 40 controls driving of the pump 30. More specifically, the controller 40 controls driving of the pump 30 such that a liquid R is retained in the closed space M and the flow passage 20, pressurization and depressurization of the liquid R in the closed space M are performed through the flow passage 20 so that the liquid R flows into and out from the closed space M a plurality of times.

The controller 40 controls driving of the pump 30 by suitably adjusting at least one of a number of times that the pressurization and the depressurization of the closed space M in which the liquid R is retained are performed through the flow passage 20, a speed of the pressurization and the depressurization, a time period during which the pressurization and the depressurization are performed, and a strength of a pressure applied to the closed space M during the pressurization or the depressurization.

More specifically, the controller 40 controls driving of the pump 30 such that repetition of the pressurization and the depressurization applied to the closed space M is not slow, that is, 1 cycle per 1 second, for example.

The controller 40 may control driving of the pump 30 such that an amount of liquid R which is used for the pressurization and the depressurization of the closed space M is determined using a pressure value of the pump 30 as a reference.

A ratio between pressurization and depressurization during the pressurization and the depressurization of the closed space M may be determined depending on the manner of removing the waste S in the closed space M from the intestine wall W.

More specifically, in order to apply forces in a plurality of directions to the waste S in the closed space M, a ratio of pressurization and a ratio of depressurization may be set to the same ratio. In order to remove the waste S from the intestine wall W by a liquid feeding force, an amount of pressurization may be set larger than an amount of depressurization. In order to remove the waste S from the intestine wall W by a suction force, an amount of depressurization may be set larger than an amount of pressurization.

As described previously, the controller 40 controls inflation and deflation of the balloons 71, 72 by controlling driving of the air feeding device 60.

Other components of the endoscope apparatus 50 are substantially equivalent to the corresponding components of the conventional endoscope apparatuses and hence, the detailed description of such other components is omitted.

Next, the operation for removing the waste S in an intestine H using the endoscope apparatus 50 which has the above described configuration is described with reference to FIG. 3 to FIG. 7.

Figure 3:
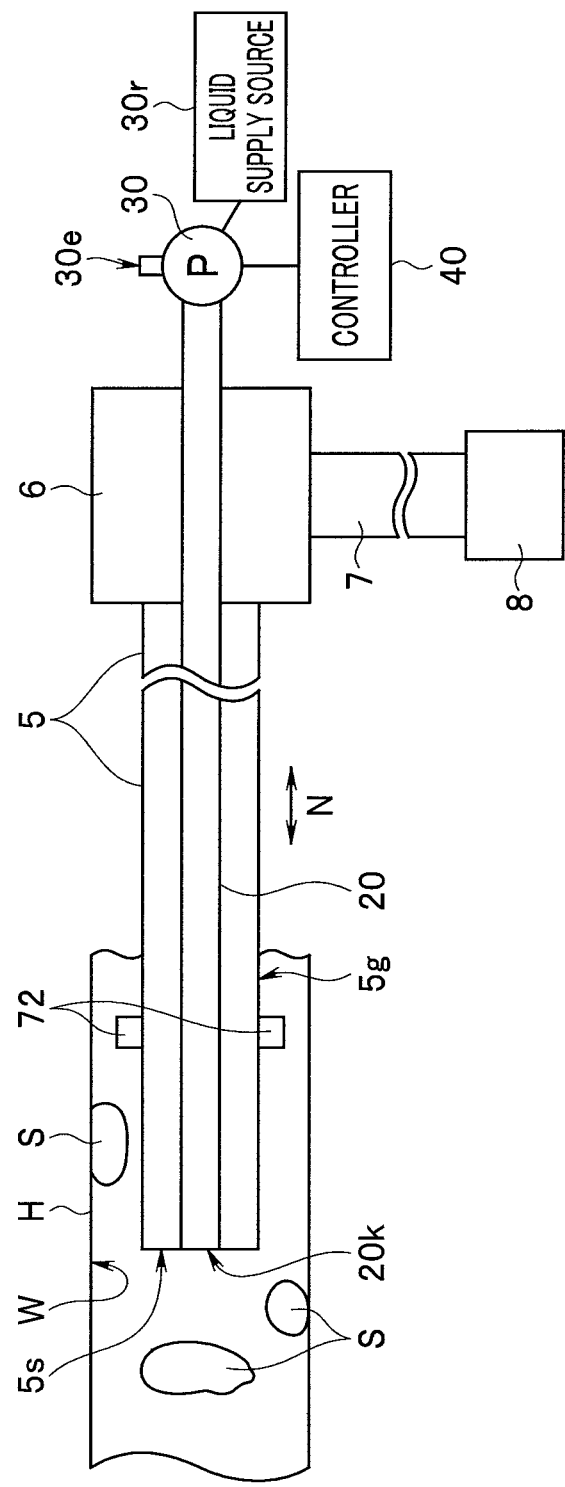
FIG. 3 is a view schematically showing a state where the insertion section shown in FIG. 1 is inserted into an intestine.
Figure 4:
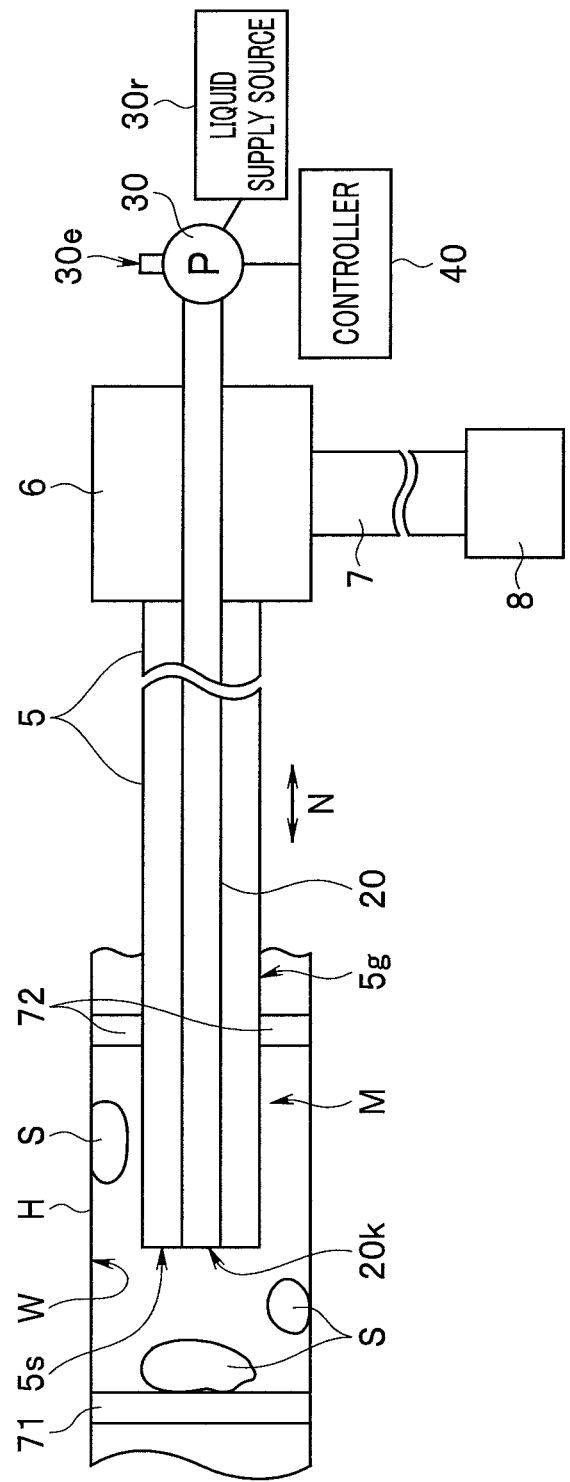
FIG. 4 is a view schematically showing a state where a closed space is formed in the intestine shown in FIG. 3 by balloons.
Figure 5:
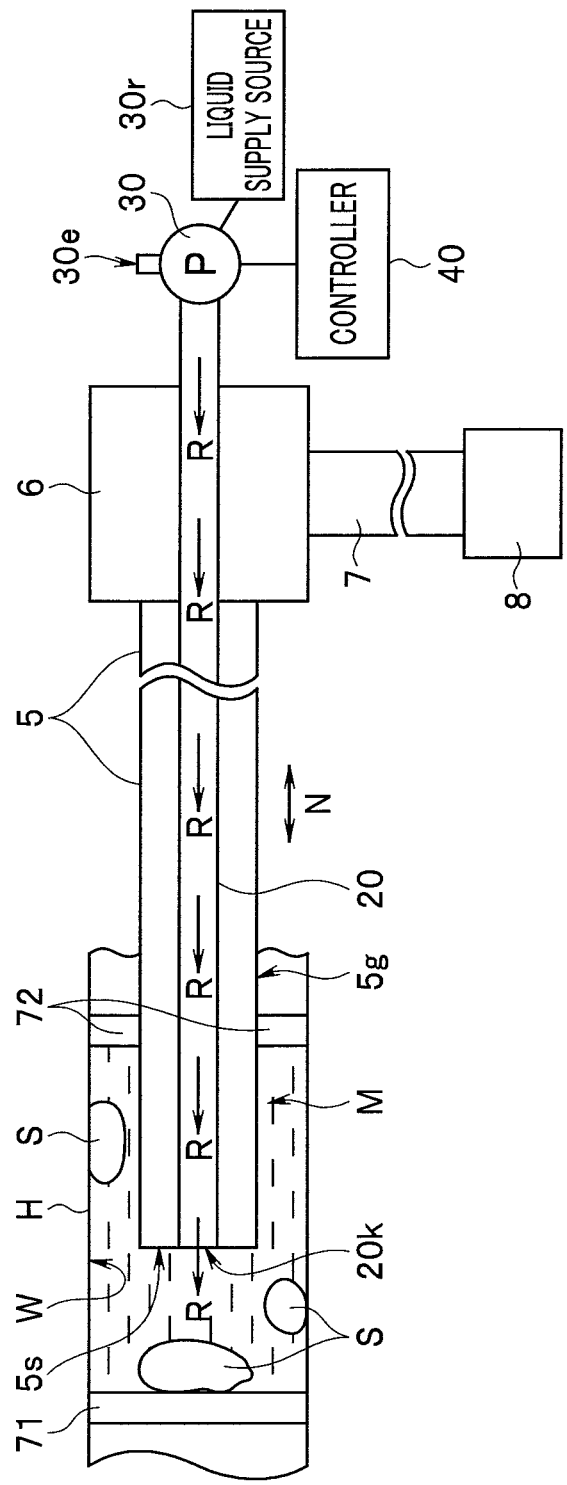
FIG. 5 is a view schematically showing a state where liquid is retained in the closed space shown in FIG. 4.
Figure 6:
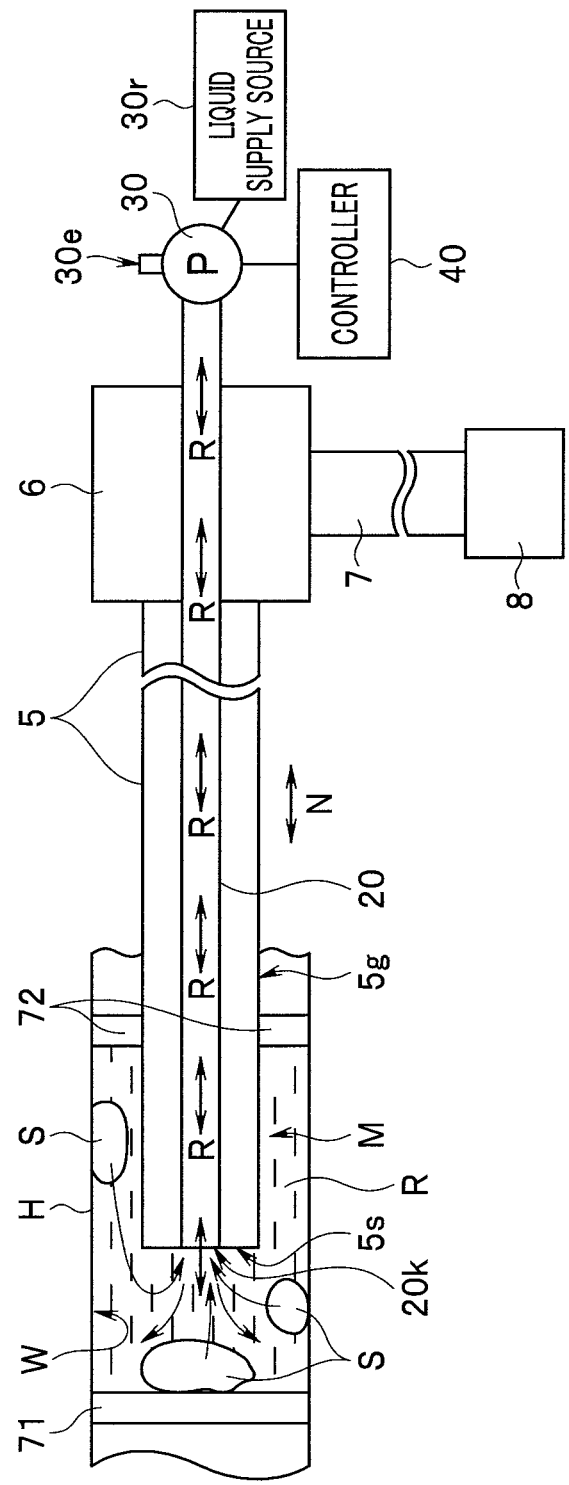
FIG. 6 is a view schematically showing a state where pressurization and depressurization of the liquid in the closed space are performed in the state where the liquid is retained in the closed space shown in FIG. 5.
Figure 7:
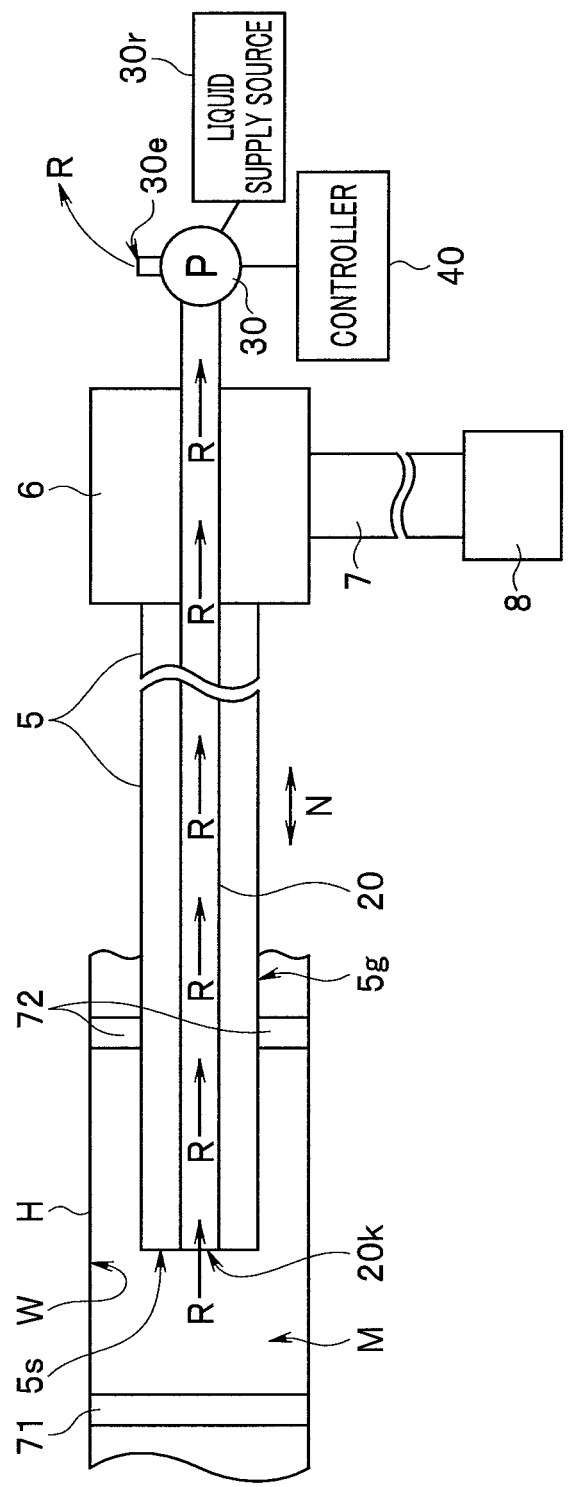
FIG. 7 is a view schematically showing a mode where the liquid retained in the closed space shown in FIG. 6 is discharged to an outside of the closed space.

FIG. 3 is a view schematically showing a state where the insertion section shown in FIG. 1 is inserted into an intestine. FIG. 4 is a view schematically showing a state where the closed space is formed in the intestine shown in FIG. 3 by the balloons. FIG. 5 is a view schematically showing a state where a liquid is retained in the closed space shown in FIG. 4. FIG. 6 is a view schematically showing a state where the pressurization and the depressurization of the liquid in the closed space are performed in the state where the liquid is retained in the closed space shown in FIG. 5. FIG. 7 is a view schematically showing a mode where the liquid retained in the closed space shown in FIG. 6 is discharged.

In cleaning the waste S in an intestine H using the endoscope apparatus 50 according to the embodiment, first, as shown in FIG. 3, a step of inserting the insertion section 5 is performed where the insertion section 5 is inserted into the intestine H from a distal end side of the insertion section 5.

Next, as shown in FIG. 4, using the previously mentioned method, the balloons 71, 72 are arranged at positions in a region of the intestine H where the waste S adhere to the intestine H as described previously with reference to FIG. 4.

Then, the balloons 71, 72 are inflated with air fed from the air feeding device 60 by drive control performed by the controller 40, and the balloons 71, 72 are brought into contact with an intestine wall W.

As a result, a step of forming a closed space M is performed. In the step, the closed space M is formed by the balloons 71, 72, and the liquid R is retained in the intestine H.

Next, as shown in FIG. 5, a step of supplying the liquid R to the closed space M is performed. In the step, the controller 40 controls driving of the pump 30 so as to flow the liquid R from the liquid supply source 30r into the closed space M through the flow passage 20. Then, a step of retaining the liquid R in the closed space M is performed.

Next, as shown in FIG. 6, in a state where the liquid R is retained in the closed space M, a step of performing pressurization and depressurization of the liquid R is performed. In the step, the pressurization and depressurization of the liquid R in the closed space M are performed a plurality of times by the pump 30 in accordance with drive control performed by the controller 40.

In such steps, as if a person fills his/her mouth with a liquid, closes his/her mouth, and gargles with the liquid, the liquid R flows into and out from the closed space M a plurality of times by performing pressurization and depressurization of the liquid R in the closed space M a plurality of times. In this manner, a flow direction of the liquid R in the closed space M changes continuously and hence, it is possible to apply a strong waste removing force to the waste S which firmly adhere to the intestine wall W by way of the liquid R. As a result, the waste S are peeled off from the intestine wall W and are mixed in the liquid R.

Finally, a step of discharging the liquid R to the outside of the endoscope 1 is performed. In the step, with drive control of the pump 30 performed by the controller 40, the liquid R retained in the closed space M to which pressurization and depressurization are applied a plurality of times through the flow passage 20 is made to flow out to the outside of the endoscope 1 from the liquid discharge opening 30e with the waste S mixed in the liquid R.

The liquid R discharged from the liquid discharge opening 30e is discharged to a tank or the like not shown with the waste S.

In this manner, in the embodiment, the endoscope apparatus 50 includes the closed space forming member 70 which forms the closed space M in the region of the intestine H where the waste S adhere to the intestine H. In the endoscope apparatus 50, in a state where the liquid R is retained in the closed space M, in accordance with drive control performed by the controller 40, the pump 30 performs the pressurization and the depressurization of the liquid R in the closed space M a plurality of times through the flow passage 20, then, discharges the liquid R in the closed space M to the outside from the liquid discharge opening 30e through the flow passage 20 with the waste S which are mixed in the liquid R.

Compared to the configuration of a conventional endoscope apparatus where a supply of a liquid R to waste S and the suction of the liquid R are repeatedly performed until the waste S are removed, the configuration of the endoscope apparatus according to the embodiment can remove waste adhering to an intestine wall W with a smaller amount of liquid. More specifically, by feeding a liquid to the closed space M only once and by making use of the water flow generated by applying the pressurization and depressurization to the liquid R in the closed space M, it is possible to remove with certainty the waste which adhere to the intestine wall W within a short time.

With such a configuration, unlike the conventional endoscope apparatuses, it is unnecessary to increase a diameter of an air supply conduit and a diameter of a liquid supply conduit in order to increase a supply pressure of the fluid supplied to the waste S, to use pressure resistant conduits each having a large wall thickness as the air supply conduit and the liquid supply conduit, or to increase a size of the air feeding device and a size of an liquid feeding device so as to increase a supply capacity. Accordingly, it is possible to prevent the increase of a diameter of the insertion section 5 and the increase of a size of the endoscope apparatus 50.

In the embodiment, the first flow passage 21 for supplying the liquid R to the closed space M, the second flow passage 22 used for pressurization and depressurization of the liquid R in the closed space M, and the third flow passage 23 used for discharging the liquid R from the closed space M are formed integrally as the flow passage 20.

With such a configuration, it is possible to allow the insertion section 5 to have a small diameter compared to a case where the flow passages 21 to 23 are separately disposed in the insertion section 5.

From the above, it is possible to provide the endoscope apparatus 50 having the configuration where the endoscope apparatus 50 can remove waste within a short time with a small amount of fluid to be supplied while preventing size increase of the endoscope apparatus and maintaining a small diameter of the insertion section 5. It is also possible to provide the method of operating the endoscope apparatus 50.

Second Embodiment

Figure 8:
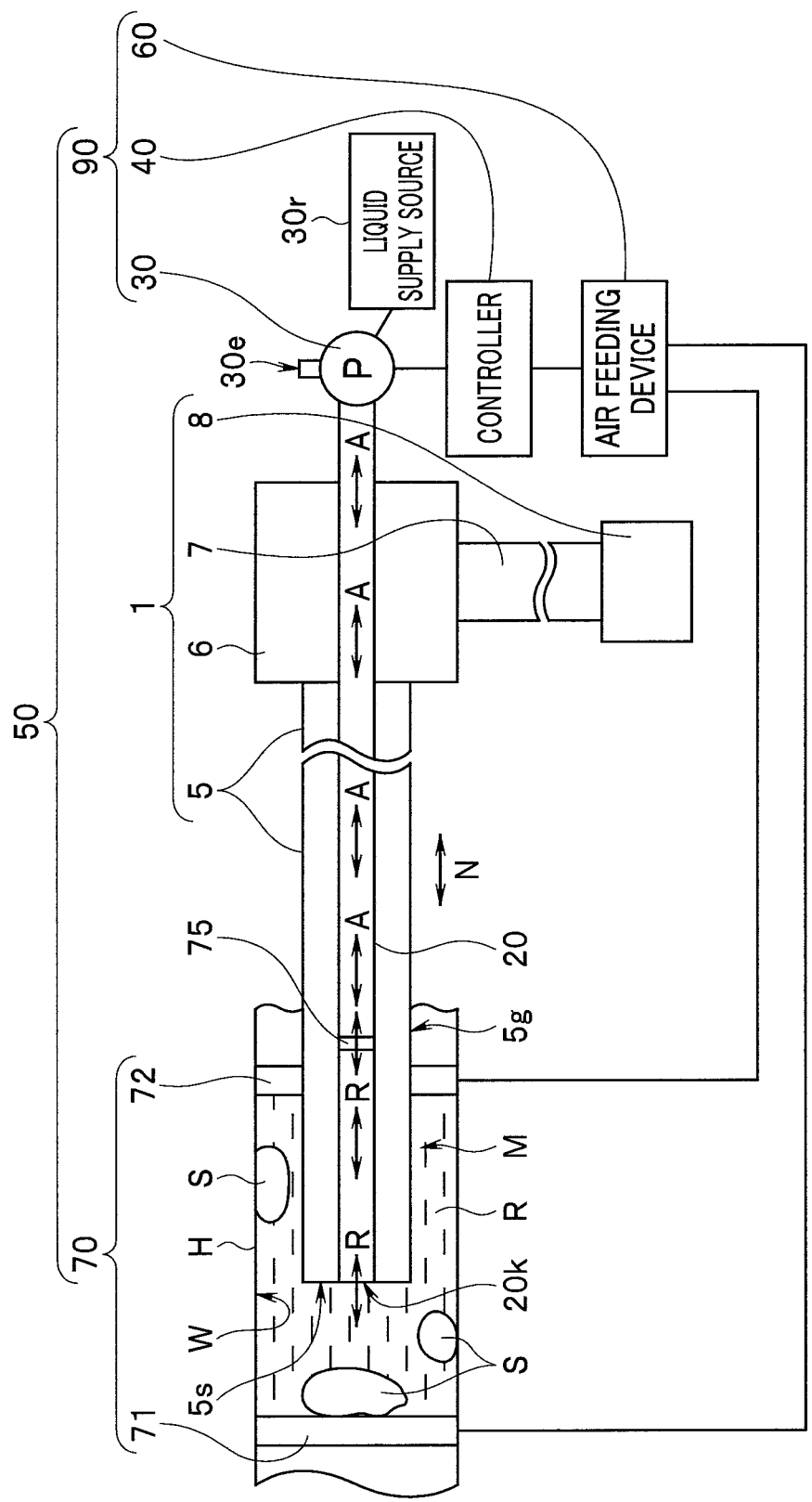
FIG. 8 is a view schematically showing an endoscope apparatus according to a second embodiment in a state where an insertion section of an endoscope is inserted into an object.

FIG. 8 is a view schematically showing an endoscope apparatus according to a second embodiment in a state where an insertion section of an endoscope is inserted into an object.

A configuration of the endoscope apparatus according to the second embodiment differs from the endoscope apparatus according to the first embodiment described with reference to FIG. 1 to FIG. 7 with respect to a point that a valve is disposed in a flow passage.

Accordingly, only different points which make the second embodiment differ from the first embodiment are described. Components substantially equivalent to the components of the first embodiment are given with the same symbols, and the description of such components is omitted.

As shown in FIG. 8, in the endoscope apparatus 50 of the embodiment, the valve 75 is disposed in a flow passage 20 formed in the endoscope 1. When the pressurization and the depressurization of a liquid R in a closed space M described in the first embodiment is performed by a pump 30, the valve 75 shuts the flow of a liquid R so as to prevent the liquid R from flowing out of an object through the flow passage 20. In other words, in the flow passage 20, the valve 75 is positioned between the closed space M and the pump 30.

The valve 75 sways frontward and rearward in a longitudinal direction N by air A supplied in the flow passage 20 on an upstream side with respect to the valve 75 from the pump 30 along with the pressurization and the depressurization of the flow passage 20 performed by the pump 30.

As a result, in the same manner as the above-mentioned first embodiment, the pressurization and the depressurization are applied to the liquid R in the closed space M a plurality of times through the valve 75.

In such a configuration, the supply and the discharge of the liquid R to and from the closed space M may be performed using, for example, the first flow passage 21 and the third flow passage 23 disposed in the sheath 80 described previously.

In the embodiment, a controller 40 may control driving of the pump 30 such that an amount of the liquid R used for pressurization and depressurization of the closed space M is determined using a moving amount of the valve 75 as a reference.

Other components are equivalent to the corresponding components of the first embodiment described above.

With such a configuration, it is possible to prevent the liquid R sucked from an opening 20k from erroneously flowing into the pump 30 by the valve 75 during the repeated pressurization and depressurization of the liquid R in the closed space M performed using the pump 30. Other advantageous effects acquired by the second embodiment are equivalent to the advantageous effects acquired by the first embodiment described above.

Hereinafter, modifications are described with reference to FIG. 9 to FIG. 11.

Figure 9:
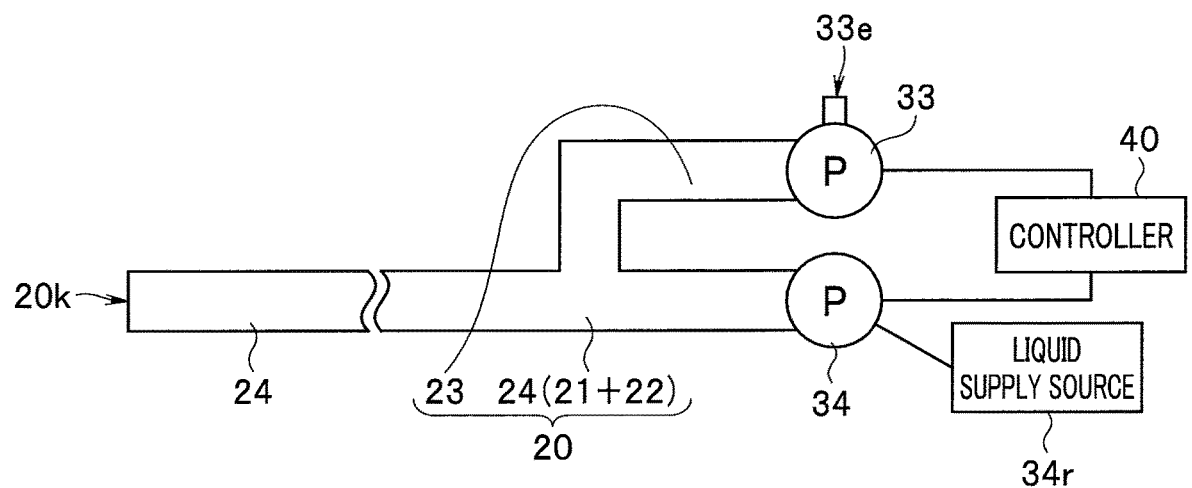
FIG. 9 is a view showing a modification of a flow passage shown in FIG. 1 where the flow passage is constituted of a fourth flow passage which is functionally shared by a first flow passage and a second flow passage, and a third flow passage branched from the fourth flow passage.

FIG. 9 is a view showing a modification of the flow passage shown in FIG. 1 where the flow passage is constituted of a fourth flow passage which is functionally shared by a first flow passage and a second flow passage, and a third flow passage branched from the fourth flow passage. FIG. 10 is a view showing a modification of the flow passage shown in FIG. 1 where the flow passage is constituted of a fifth flow passage which is functionally shared by a second flow passage and a third flow passage, and a first flow passage branched from the fifth flow passage. FIG. 11 is a view showing a modification of the flow passage shown in FIG. 1 where the flow passage is constituted of a second flow passage, a first flow passage branched from the second flow passage, and a third flow passage branched from the second flow passage.

In the above mentioned first and second embodiments, the configuration is described where one flow passage 20 is formed so as to function as the first flow passage 21, the second flow passage 22 and the third flow passage 23.

The present embodiment is not limited to such a configuration. As shown in FIG. 9, the flow passage 20 may be constituted of: the fourth flow passage 24 which is functionally shared by the first flow passage 21 and the second flow passage 22; and the third flow passage 23 which is branched from the fourth flow passage 24 and is connected to a pump 33 for suction. The pump 33 for suction includes a liquid discharge opening 33e which constitutes a fluid discharge passage. The fourth flow passage 24 is connected to a pump 34 which is used for supplying a liquid R from a fluid supply source 34r and for pressurization and depressurization of the liquid R in a closed space M.

In such a configuration, the third flow passage 23 and a portion of the fourth flow passage 24 downstream of a merging point where the fourth flow passage 24 merges with the third flow passage 23 constitutes a fluid discharge passage.

In such a configuration, for example, by constituting the third flow passage 23 as a separably disposable tube, only the third flow passage 23 which is contaminated by suction after cleaning the closed space M can be easily discarded and replaced.

In a configuration obtained by providing the valve 75 in the second embodiment to the configuration shown in FIG. 9, the valve 75 may be disposed in the fourth flow passage 24.

Figure 10:
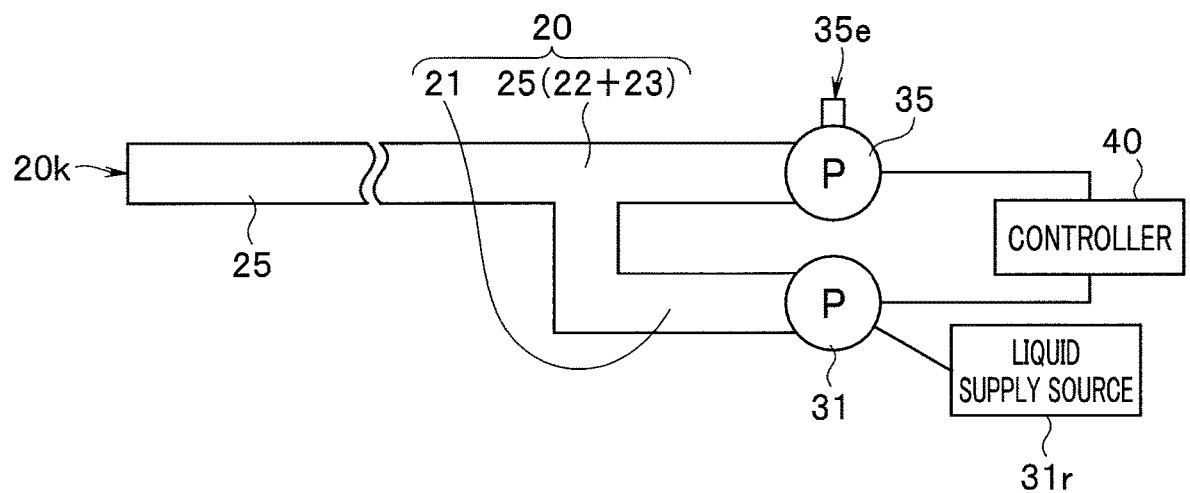
FIG. 10 is a view showing a modification of the flow passage shown in FIG. 1 where a flow passage is constituted of a fifth flow passage which is functionally shared by a second flow passage and a third flow passage, and a first flow passage branched from the fifth flow passage.

As shown in FIG. 10, the flow passage 20 may be constituted of, the fifth flow passage 25 which is functionally shared by the third flow passage 23 and the second flow passage 22; and the first flow passage 21 which is branched from the fifth flow passage 25 and to which a pump 31 for supplying liquid which is connected to a liquid supply source 31r is connected. The fifth flow passage 25 is connected to a pump 35 which discharges a liquid R from a liquid discharge opening 35e which constitutes a fluid discharge passage and is used for pressurization and depressurization of the liquid R in the closed space M.

In a configuration obtained by providing the valve 75 in the second embodiment to the configuration shown in FIG. 10, the valve 75 may be disposed in the fifth flow passage 25. In such a configuration, the fifth flow passage 25 constitutes a fluid discharge passage.

Figure 11:
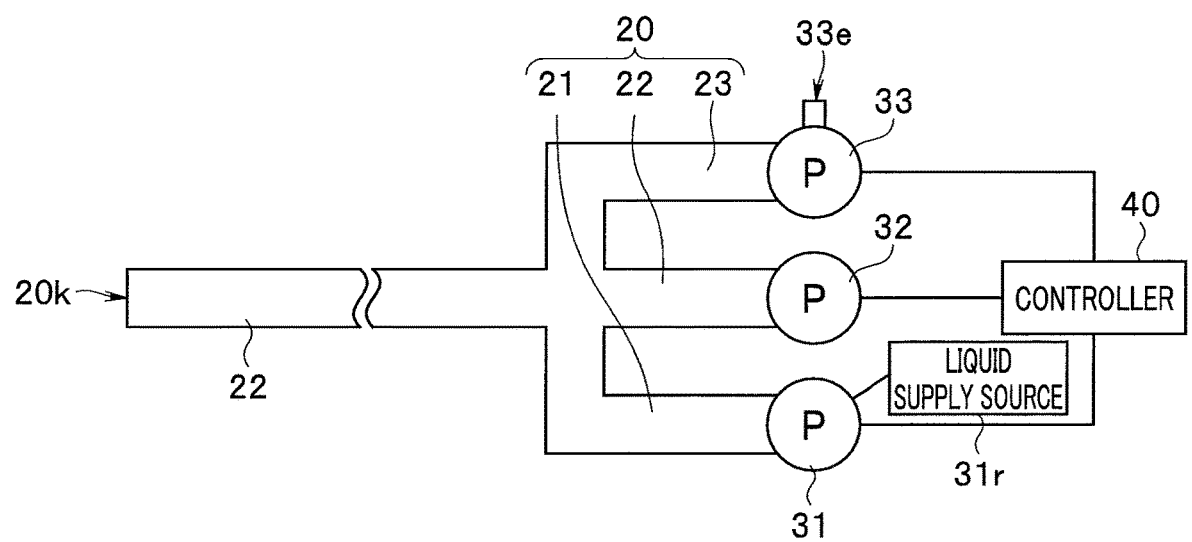
FIG. 11 is a view showing a modification of the flow passage shown in FIG. 1 where the flow passage is constituted of a second flow passage, a first flow passage branched from the second flow passage, and a third flow passage branched from the second flow passage.

As shown in FIG. 11, the flow passage 20 may be constituted of: the second flow passage 22 which is connected to a pump 32 used for pressurization and depressurization of a liquid R in a closed space M; the first flow passage 21 which is branched from the second flow passage 22 and is connected to a pump 31 for supplying liquid; and the third flow passage 23 which is branched from the second flow passage 22 and is connected to a pump 33 for discharging liquid having the liquid discharge opening 33e.

In a configuration obtained by providing the valve 75 in the second embodiment to the configuration shown in FIG. 11, the valve 75 may be disposed in the second flow passage 22.

In such a configuration, the third flow passage 23 and a portion of the second flow passage 22 downstream of a merging point where the first flow passage 21 and the third flow passage 23 merge with the second flow passage 22 constitute a fluid discharge passage.

In other words, at least some of the first flow passage 21, the second flow passage 22 and the third flow passage 23 may be formed as a separate flow passage.

At least one of the first flow passage 21 and the third flow passage 23 may be branched from an intermediate portion of the second flow passage 22.

The branched configuration where the first flow passage 21 and the third flow passage 23 are branched from the second flow passage 22 is not limited to the configurations shown in FIG. 9 to FIG. 11 described above, and various configurations can be considered. The above-mentioned first and second embodiments are applicable to the branched configurations shown in FIG. 9 to FIG. 11 and all other various branched configurations.

Figure 12:
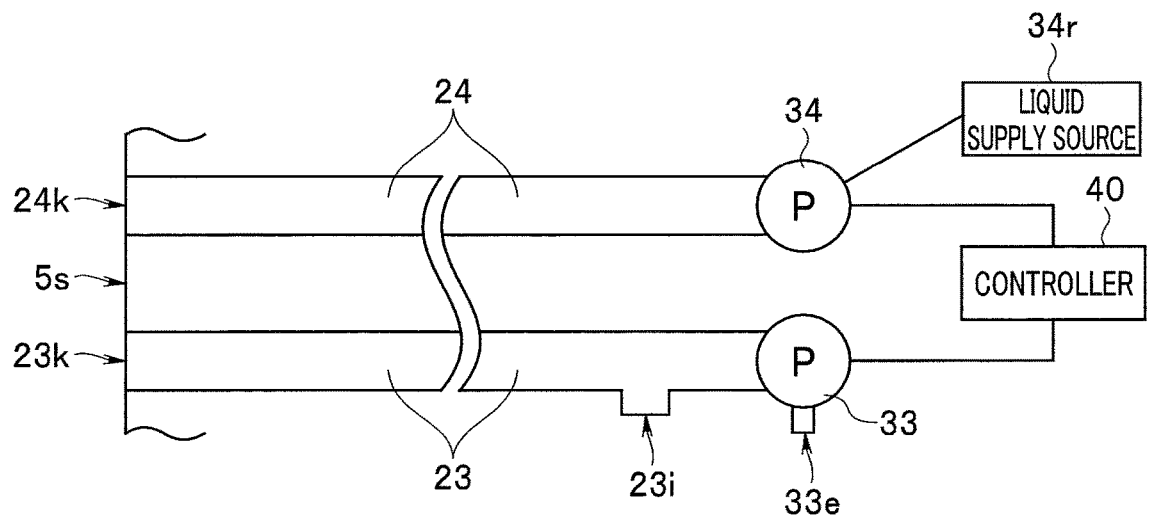
FIG. 12 is a view showing a modification of the third flow passage shown in FIG. 9 where a third flow passage is formed independently without being branched from a fourth flow passage.

Hereinafter, another modification is described with reference to FIG. 12. FIG. 12 is a view showing a modification where the third flow passage shown in FIG. 9 is not branched from a fourth flow passage and is formed separately from the fourth flow passage.

As shown in FIG. 12, a first flow passage 21 and a second flow passage 22 may be provided integrally as the fourth flow passage 24, and a third flow passage 23 may not be branched from the fourth flow passage 24, and may be provided separately from the fourth flow passage 24.

In other words, the third flow passage 23 may be provided separately from the fourth flow passage 24 which has an opening 24k at a distal end surface 5s so as to have an opening 23k at the distal end surface 5s.

In such a configuration, the third flow passage 23 used for suction is provided as a single flow passage. Accordingly, as described previously, the third flow passage 23 may also function as a treatment instrument insertion conduit having a treatment instrument insertion opening 23i.

Although not shown, the second flow passage 22 and the third flow passage 23 may be provided integrally as the fifth flow passage 25, and the first flow passage 21 may be provided separately from the fifth flow passage 25. Alternatively, one flow passage may function as the first flow passage 21 and the third flow passage 23, and the second flow passage 22 may be provided separately from the one flow passage.

Figure 13:
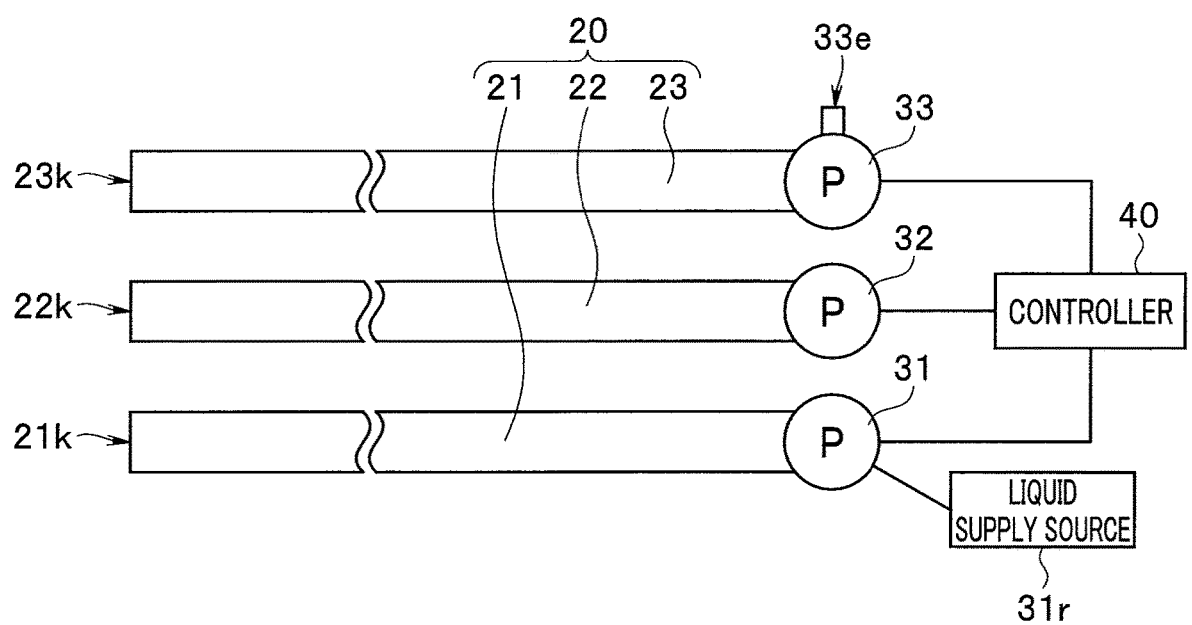
FIG. 13 is a view showing a modification of the flow passage shown in FIG. 1 where the flow passage is constituted of first to third flow passages which are formed independently from each other.

Hereinafter, still another modification is described with reference to FIG. 13. FIG. 13 is a view showing a modification of the flow passage shown in FIG. 1 where a flow passage is constituted of first to third flow passages which are formed independently from each other.

As shown in FIG. 13, the flow passage 20 may be constituted of the first flow passage 21 to the third flow passage 23 which are formed as separate flow passages respectively. The first flow passage 21 to the third flow passage 23 respectively include openings 21k to 23k at a distal end surface 5s, and are respectively connected to pumps 31 to 33.

Hereinafter, still another modification is described.

In the above-mentioned first and second embodiments, the case is exemplified where the closed space forming member 70 is constituted of the balloons 71, 72. However, the present invention is not limited to such a configuration. The closed space forming member 70 may be constituted of only the balloon 71, or only the balloon 72 provided that the closed space M which can retain the liquid R can be formed in the intestine H. The present invention is also applicable to a case where the closed space M can be formed in the intestine H without using the closed space forming member 70.

Hereinafter, still another modification is described.

As the above-mentioned method of removing the waste S using the endoscope apparatus 50, various methods may be adopted.

More specifically, in a case where an excessively large amount of waste S adheres to an intestine H, the following method may be adopted. First, in the same manner as the prior art, the feeding of a liquid to waste S and the suction of the liquid are repeatedly performed so as to dissolve soft portions of the waste S and, then, the method which is previously described in the first or second embodiment is repeatedly performed so as to remove the waste S.

Alternatively, first, a liquid, a liquid mixed with air, or a liquid, an acceleration force of which is increased by air, is supplied to waste S and, then, in a case where the waste S still cannot be removed from an intestine wall W, the method which is previously described in the first or second embodiment may be repeatedly performed so as to remove the waste S.

The above-mentioned first and second embodiments are also applicable to combinations obtained by combining the embodiments with other various kinds of methods of removing waste S.

In the above-mentioned first and second embodiments, the case is exemplified where the insertion section 5 is inserted into the intestine H of a large intestine. However, the present invention is not limited to such a case. It goes without saying that the present invention is applicable to a case where the insertion section 5 is inserted into a body cavity other than the intestine and cleaning of waste in the body cavity is performed.

In the above-mentioned first and second embodiments, an endoscope apparatus for medical use having functions such as removing the food residue adhering to the inner wall of the large intestine is exemplified as the endoscope apparatus 50. However, the present invention is not limited to such an endoscope apparatus. It goes without saying that the present invention is applicable to an endoscope apparatus for industrial use having functions such as removing waste strongly adhering to an inside of a conduit.

According to the present invention, it is possible to provide an endoscope apparatus having a configuration in which the endoscope apparatus can remove waste quickly with a small amount of fluid to be supplied while preventing the endoscope apparatus from increasing in size and maintaining a small diameter of the insertion section. According to the present invention, it is also possible to provide a method of operating the endoscope apparatus.

The present invention is not limited to the above-mentioned embodiments, and can be appropriately modified without departing from the gist or concept of the present invention read from claims, the entire specification, and drawings.

What is claimed is:

1. An endoscope apparatus comprising:
a first ballon configured to form a closed space;
an insertion section on which the first balloon is mounted, the insertion section being configured to define:
an opening; and
a flow passage communicating through the opening with an inside of the closed space;
a pump; and
a controller configured to:
control the pump to feed a fluid through the flow passage into the closed space;
while the fluid is retained in the closed space formed by the first balloon, perform drive control of the pump to switch between applying pressurization and depressurization to the flow passage a plurality of times to repeatedly change a flow direction of the fluid retained in the closed space, wherein the fluid is suctioned through the flow passage and supplied through the flow passage repeatedly without the fluid draining out from both of the flow passage and the closed space; and
after performing the drive control, control the pump to discharge the fluid out of the closed space through the flow passage.

2. The endoscope apparatus according to claim 1, wherein the flow passage comprises:
a first flow passage configured to feed the fluid to the closed space;
a second flow passage through which the pump applies the pressurization and the depressurization to change the flow direction of the same fluid retained in the closed space; and
a third flow passage configured to discharge the fluid from the closed space.

3. The endoscope apparatus according to claim 2, wherein at least a portion of the first flow passage, at least a portion of the second flow passage and at least a portion of the third flow passage are formed integrally so as to have a common conduit.

4. The endoscope apparatus according to claim 3, wherein at least one of the first flow passage and the third flow passage is branched from an intermediate portion of the second flow passage.

5. The endoscope apparatus according to claim 2, wherein the first flow passage, the second flow passage and the third flow passage are formed as separate flow passages respectively.

6. The endoscope apparatus according to claim 1, wherein the flow passage is configured to receive a treatment instrument.

7. The endoscope apparatus according to claim 1, further comprising:
a second balloon configured to, with the first balloon, form the closed space.

8. The endoscope apparatus according to claim 1, further comprising:
a valve arranged between a distal end and a proximal end of the insertion section, the valve being configured to prevent the fluid that has been fed into the closed space from flowing from the distal end to the proximal end of the insertion section when the pressurization and the depressurization are applied the plurality of times.

9. The endoscope apparatus according to claim 1, wherein the controller is configured to perform the drive control of the pump by adjusting at least one of:
a number of times that the pressurization and the depressurization is performed;
a speed of the pressurization and the depressurization;
a time period during which the pressurization and the depressurization are performed; and
a strength of a pressure applied during the pressurization or the depressurization.

10. The endoscope apparatus according to claim 8, wherein the pump is configured to cause the valve to sway frontward and rearward in a longitudinal direction of the flow passage to prevent the fluid that has been fed into the closed space from flowing from the distal end to the proximal end of the insertion section when the pressurization and the depressurization are applied the plurality of times.

11. The endoscope apparatus according to claim 1, wherein the pump comprises a first pump and a second pump, and
wherein the flow passage comprises:

a common conduit having a first end leading to the opening, and a second end;

a branch communicating with the second end of the common conduit;

a first conduit communicating with the common conduit via the branch and connected to the first pump; and a second conduit communicating with the common conduit via the branch and connected to the second pump, wherein the second pump is configured to switch between applying the pressurization and the depressurization to the second conduit and the common conduit the plurality of times to repeatedly change the flow direction of the same fluid retained in the closed space.

12. The endoscope apparatus according to claim 11, further comprising:

a valve arranged between the first end and the second end of the common conduit, the valve being configured to prevent the fluid that has been fed into the closed space from flowing from the first end to the second end of the common conduit when the pressurization and the depressurization are applied the plurality of times.

13. The endoscope apparatus according to claim 11, wherein the first pump is configured to perform one of a first process of feeding the fluid through the opening into the closed space and a second process of discharging the fluid from the closed space, through the common conduit and the first conduit, and wherein the second pump is configured to perform the other of the first process and the second process, through the common conduit and the second conduit.

14. The endoscope apparatus according to claim 11, wherein the pump further comprises a third pump, wherein the flow passage further comprises a third conduit communicating with the common conduit via the branch and connected to the third pump, wherein the first pump is configured to feed the fluid through the opening into the closed space through the common conduit and the first conduit, and wherein the third pump is configured to discharge the fluid from the closed space through the common conduit and the third conduit.

15. An endoscope apparatus comprising:

a closed space forming member configured to form a closed space in at least a portion in an object such that a fluid is retained in the object;

an insertion section configured to be inserted into the object from a distal end side of the insertion section in a longitudinal direction, wherein the insertion section defines:

an opening; and a flow passage communicating through the opening with an inside of the closed space; a pump; and a controller configured to:

control the pump to feed a fluid through the flow passage into the closed space;

while the fluid is retained in the closed space formed by the closed space forming member, perform drive control of the pump to switch between applying pressurization and depressurization to the flow passage a plurality of times to repeatedly change a flow direction of the fluid retained in the closed space, wherein the fluid is suctioned through the flow passage and supplied through the flow passage repeatedly without the fluid draining out from both of the flow passage and the closed space; and after performing the drive control, control the pump to discharge the fluid out of the closed space through the flow passage.

16. The endoscope apparatus according to claim 1, wherein the closed space is formed in part by an outer surface of the first balloon.

17. The endoscope apparatus according to claim 7, wherein the second balloon is provided distally relative to the first balloon.

18. The endoscope apparatus according to claim 1, wherein the insertion section is configured to be inserted into a tubular organ, and wherein the closed space is formed in part by a wall of the tubular organ.

* * * * *